(12) United States Patent
Groten et al.

(10) Patent No.: US 7,410,555 B2
(45) Date of Patent: Aug. 12, 2008

(54) PROCESS AND APPARATUS FOR CATALYTIC DISTILLATIONS

(75) Inventors: Willibrord A. Groten, Houston, TX (US); Mario J. Maraschino, Kingwood, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 0 days.

(21) Appl. No.: 10/839,398

(22) Filed: May 5, 2004

(65) Prior Publication Data

US 2004/0210090 A1 Oct. 21, 2004

Related U.S. Application Data

(62) Division of application No. 10/167,196, filed on Jun. 11, 2002, now Pat. No. 6,930,206.

(60) Provisional application No. 60/303,233, filed on Jul. 5, 2001.

(51) Int. Cl.
*B01D 3/14* (2006.01)
*B01D 3/40* (2006.01)

(52) U.S. Cl. .................. 202/153; 202/158; 203/29; 203/50

(58) Field of Classification Search ............... 202/153, 202/158; 203/29, 28, 50, DIG. 6; 196/111; 422/211

See application file for complete search history.

(56) References Cited

U.S. PATENT DOCUMENTS

| 1,661,827 | A | * | 3/1928 | Hessle et al. | 422/195 |
| 4,028,191 | A |   | 6/1977 | Scott | 202/158 |
| 4,215,011 | A | * | 7/1980 | Smith, Jr. | 422/211 |
| 4,230,533 | A |   | 10/1980 | Giroux | 203/1 |
| 4,242,530 | A |   | 12/1980 | Smith, Jr. | 585/510 |

(Continued)

FOREIGN PATENT DOCUMENTS

JP 09299701 * 11/1997

*Primary Examiner*—Virginia Manoharan
(74) *Attorney, Agent, or Firm*—Osha Liang LLP

(57) ABSTRACT

A process for reacting a first component with itself or a second component to produce a third component in which a first material comprising a first component or said first component and a second component is fed to divided wall column having a catalytic distillation structure in at least one of the separate vertical sections of the divided wall column where concurrently: (1) a first component alone or with a second component is contacted with a catalytic distillation structure in a distillation reaction zone thereby catalytically reacting at least a portion of the first component with itself or with the second component to form a product and (2) a first mixture comprising the first component and the product or the first component, the second component and the product; and withdrawing the product from the distillation column reactor; while within the column concurrently with the catalytic reaction and fractionation a second mixture is fractionated, which contains the first component and the product or first and second components (if a second component is present) and the product in a parallel and separate distillation non reaction zone to fractionate the product and withdrawing the product from said distillation non reaction zone. For example, tertiary amyl methyl ether may be prepared by reacting methanol with isoamylene in a $C_5$ stream utilizing a distillation column reactor wherein the distillation column reactor comprises one side of a divided wall column. On one side the product, tertiary amyl methyl ether, is separated from the unreacted methanol and $C_5$'s and on the other side the remaining isoamylenes are reacted with methanol and a separation of the tertiary amyl methyl ether and $C_5$'s from the methanol/$C_5$ azeotrope is effected.

4 Claims, 2 Drawing Sheets

U.S. PATENT DOCUMENTS

| | | | |
|---|---|---|---|
| 4,504,687 A | 3/1985 | Jones, Jr. | 568/697 |
| 4,582,569 A | 4/1986 | Jenkins | 202/158 |
| 4,826,574 A | 5/1989 | Gourlia et al. | 202/158 |
| 5,215,725 A * | 6/1993 | Sy | 422/212 |
| 5,339,648 A | 8/1994 | Lockett et al. | 62/24 |
| 5,395,981 A * | 3/1995 | Marker | 568/697 |
| 5,523,061 A * | 6/1996 | Hao et al. | 422/191 |
| 5,709,780 A | 1/1998 | Ognisty et al. | 202/158 |
| 5,755,933 A | 5/1998 | Ognisty et al. | 202/158 |
| 6,254,735 B1 * | 7/2001 | Watzenberger | 203/26 |
| 6,347,533 B1 | 2/2002 | Tung | 62/620 |
| 6,358,373 B1 * | 3/2002 | Leemann et al. | 203/29 |
| 6,387,222 B1 * | 5/2002 | Tragut et al. | 203/2 |
| 6,416,658 B1 * | 7/2002 | Maraschino et al. | 208/189 |
| 6,514,387 B1 * | 2/2003 | Emmrich et al. | 202/153 |
| 6,551,465 B1 * | 4/2003 | Van Zile et al. | 202/158 |
| 6,582,564 B2 * | 6/2003 | Tamura et al. | 202/153 |
| 6,645,350 B1 * | 11/2003 | Steacy | 202/158 |
| 2003/0181772 A1 * | 9/2003 | Meyer et al. | 585/324 |

* cited by examiner

PROCESS AND APPARATUS FOR CATALYTIC DISTILLATIONS

This is a division of application Ser. No. 10/167,196, filed on Jun. 11, 2002, now U.S. Pat. No. 6,930,206 which claims the benefit of Provisional Application 60/303,233, filed Jul. 05, 2001.

BACKGROUND OF THE INVENTION

1. Field of the Invention

The present invention relates to an apparatus and the method for carrying out catalytic distillations using a divided wall column, for example the etherification of isoolefins, particularly $C_5$ isoolefins with methanol to produce the corresponding tertiary ether, wherein catalytic distillation is used in a divided wall catalytic distillation reactor to simultaneously separate tertiary amyl methyl ether (TAME) and react substantially all of the methanol to preclude the use of a separate methanol recovery system.

2. Related Information

A divided wall distillation column or divided wall column is a distillation vessel having a vertical partition separating one side from the other for a portion or all of the height of the vessel. The divided wall column may have a common rectification section, a common stripping section or both. Such divided wall columns are variously described in U.S. Pat. Nos. 4,230,533; 4,582,569; 4,826,574; 5,339,648 and 5,755,933. Engineering design methods are assumed to be used to assure proper distribution of upflowing vapor to the alternate sides of a divided-wall column. Such methods to control vapor split may be active or passive. Also, engineering design methods are assumed to assure the proper controlled split of the liquid to both sides of a divided wall device. Such splits are purposely targeted to accomplish specific design objectives as determined from rigorous simulation analysis of the intended operation.

A specialized use of a distillation column, known as catalytic distillation has been used in etherifications, hydrogenations, hydrodesulfurizations, isomerizations, thioetherifications, oligomerizations and others. The catalytic distillation process employs a catalyst system (see U.S. Pat. Nos. 4,215,011 and 4,302,356) which provides for both reaction and distillation concurrently in the same reactor, at least in part within the catalyst system. The method involved is briefly described as one where concurrent reaction and distillation occur in a combination reactor-distillation structure as described in several U.S. Patents, namely U.S. Pat. Nos. 4,242,530; 4,250,052; 4,232,177; 4,302,356; 4,307,254; and 4,336,407.

The reaction of an alcohol and an olefin and concurrent separation of the reactants from the reaction products by fractional distillation has been practiced for some time. The process is variously described in several of the previously cited patents and U.S. Pat. Nos. 4,504,687; 4,987,807; and 5,118,873.

As an example, in a catalytic distillation etherification system the alcohol and isoolefin are fed to a distillation column reactor having a distillation reaction zone containing suitable catalyst, such as an acid cation exchange resin, preferably in the form of catalytic distillation structure, and also preferably, having a distillation zone containing an inert distillation structure, e.g., trays, saddles, and the like. As embodied in the etherification of $iC_4^=$'s and/or $iC_5^=$'s the olefin and an excess of methanol may be first fed to a straight pass reactor wherein most of the olefin is reacted to form the corresponding ether, methyl tertiary butyl ether (MTBE) or tertiary amyl methyl ether (TAME). The feeds may contain both normal and iso olefins. The reaction is highly selective toward the isoolefins. The straight pass reactor is preferably operated at a given pressure such that the reaction mixture is at the boiling point, thereby limiting the temperature rise across the reactor by permitting the exothermic heat of reaction to partially vaporize the mixture. A straight pass reactor and process are described more completely in U.S. Pat. No. 4,950,803 which is hereby incorporated by reference.

The effluent from the first reactor is then fed to a distillation column reactor wherein the unreacted isoolefins are converted to ether, the excess methanol and unreacted hydrocarbons are withdrawn as an overhead product while the ether is withdrawn as bottoms product stream.

As noted above, in the etherification of olefins with an alcohol there is preferably an excess of the alcohol available. This excess alcohol is typically recovered from the overhead stream in downstream units.

In the case of the $C_5$'s system the overhead product will contain the azeotropic level of MeOH which is about 12 wt %. If the net flow of methanol into the column (allowing for that reacting in the column) is less than the azeotrope concentration in the distillate, the methanol concentration in the reaction distillation zone will be relatively quite low, about 1%. If the net methanol flow into the column is higher than the azeotrope, the methanol concentration will increase (60% has been measured) until methanol leaves with the TAME bottoms product. Neither case is desirable because at low concentration the conversion of isoamylene to TAME is low whereas at high concentrations the TAME purity is affected by the presence of the excess methanol.

The methanol feed is thus best controlled to produce the highest methanol concentration within the catalyst bed while preventing methanol leaving with the bottoms product. This results in close to the azeotropic concentration in the distillate product and in the reaction distillation zone. The methanol must be separated from the hydrocarbons so that the hydrocarbons can be used for gasoline blending and to conserve methanol. The separation is usually achieved by washing the hydrocarbon/methanol mixture with water. The methanol is selectively absorbed in the water phase which is subsequently fractionated to separate the methanol.

The recovery of the methanol requires considerable amounts of water energy and significant number of theoretical stages which substantially increases the operating and capital cost of the process. It is an advantage of the present invention that in an etherification embodiment wherein an alcohol azeotrope is formed an alcohol recovery section is not required. It is a further advantage of the present invention that the alcohol/hydrocarbon azeotrope is maintained throughout essentially all of the reaction distillation zone, maximizing conversion of the reactive olefins.

SUMMARY OF THE INVENTION

Briefly, the present invention is a distillation column having at least two vertical distillation sections, at least one of said sections containing catalyst, preferably in a form to serve as distillation structure, and at least one of said sections being free of catalyst and the process of concurrently carrying out the reactions of a material with itself or other materials to produce products thereof and fractional separation of the product and the starting materials therein. The sections are separated by a wall extending through a vertical portion of the distillation column. The vertical portion of the separating wall comprises less than the total height of the column. The vertical wall preferably extends across the lateral dimension of the column and may extend vertically to either the top or to the bottom of the column or to neither. The sections are in fluid communication around a vertical terminus either at the upper end or the bottom end of the vertical wall or both. Thus the present apparatus provides an integrated distillation and catalytic distillation system.

The apparatus of the present invention may be characterized as a catalytic distillation column having three internal sections, at least one of said sections containing catalyst, two of said sections being separated by a vertical wall extending through a portion of said catalytic distillation column, said parallel sections being in communication above and/or below said vertical wall. Preferably, the sections include a common rectification section above the vertical wall and two parallel sections which are a simple distillation section and the other contains a catalytic distillation zone. In a further embodiment, a common stripping section is included below the vertical wall to the catalytic distillation column.

The present process may be used for reacting a first component with itself or a second component to produce a product and comprises: (a) feeding a first material comprising a first component or said first component and a second component to a distillation column reactor; (b) concurrently: (1) contacting said first component or first component and said second component with a catalytic distillation structure in a distillation reaction zone thereby catalytically reacting at least a portion of said first component with itself or said first and second components to form a product and (2) fractionating a first mixture comprising said first component and said product or said first component, said second component and said product; and (c) withdrawing product from the distillation column reactor; wherein the improvement comprises concurrently with (a) and (b) in said distillation reaction column: contacting a second mixture comprising said first component and said product or said first component, said second component and said product with a non catalytic distillation structure in a parallel and separate distillation non reaction zone to fractionate said third component product and withdrawing said third component product from said distillation non reaction zone.

In a $C_5$ etherification the first section is operated under conditions of temperature and pressure to separate any ether in the feed to the column and to fractionate hydrocarbons, including any unreacted isoolefins overhead with any alcohol as an azeotrope. The alcohol is consumed in the second section or removed from the overhead condensate.

For the purposes of the present invention, the term "catalytic distillation" includes any process of concurrent reaction and fractional distillation in a column regardless of the designation applied thereto. Several different arrangements have been disclosed to achieve the desired result. For example, British Patents 2,096,603 and 2,096,604 disclose placing the catalyst on conventional trays within a distillation column. A series of U.S. patents, including particularly U.S. Pat. Nos. 4,443,559 and 4,215,011, exemplify using the catalyst as part of the packing in a packed distillation column.

DETAILED DESCRIPTION OF THE PREFERRED EMBODIMENTS

Figure 1:
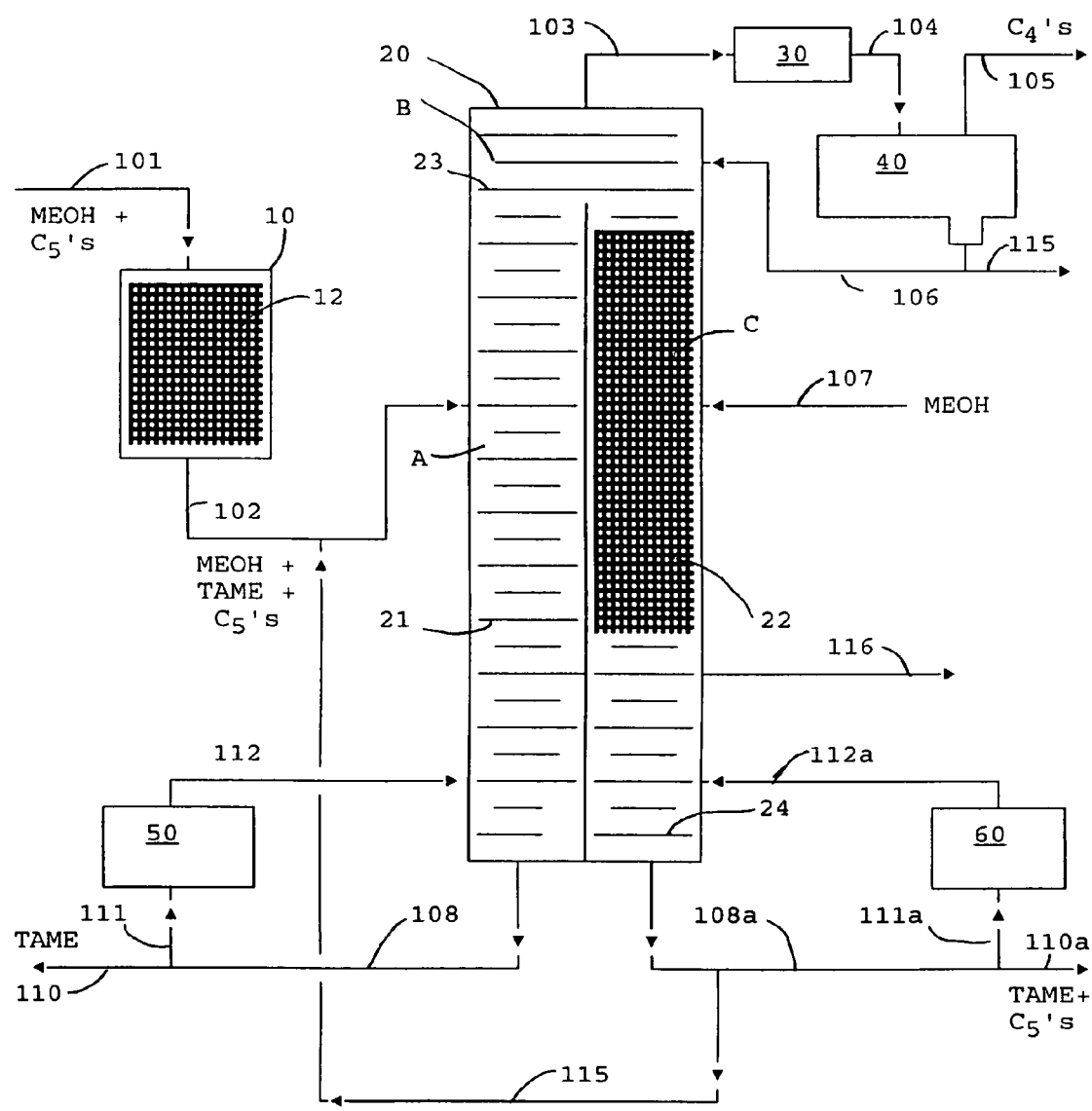
FIG. 1 is a schematic representation of the present apparatus used for the synthesis of a TAME according to present invention.

The use of a divided wall distillation column in a catalytic distillation is not heretofore described in the art. The feed to the present divided wall catalytic distillation column reactor may be from a prior reactor in which less than all of the reactants were reacted. The feed material contains the reactants and product which is fed to a non reaction distillation section to separate the product and allow the reactants to be further reacted in the catalytic distillation section to produce more product. Makeup material may be added as required. The present divided wall catalytic distillation column reactor may also be used as the primary reactor in which the reactants are fed to the catalytic distillation section and fractionated in both vertical sections. There may be a common rectification section above the divided vertical sections or a common stripping section below or both.

The operation of the present invention is described for etherification, however, the use of the divided wall column is also suitable for the other reactions, including those presently carried out under catalytic distillation conditions.

In the reactions the first component may react with itself, such as the production of a dimer from the reaction of olefin with itself or with a second component such as the reaction of an olefin with an alcohol.

Among the suitable reactions are:

oligomerization of olefins such as dimerization and the reaction of the dimers with olefins or other dimers of single olefins or mixtures of olefins, such as the oligomerization of isobutene;

reaction of alcohols to produce diethers such as the reaction of methanol with itself to form dimethyl ether;

etherification of olefins with alcohols to produce ethers;

thioetherification of dienes with mercaptans to produce sulfides;

skeletal isomerization of olefins with or without hydrogen;

position isomerization of olefins with or without hydrogen:

reaction of mercaptans and thiophenes with hydrogen to produce $H_2S$;

reaction of acetylenes, dienes, olefin or mixtures with hydrogen;

reaction of cyclic olefins and aromatic compounds with hydrogen;

reaction of aromatic compounds and alkane derivative compounds with ammonia to form amines;

reaction of nitriles with a hydration compound;

reaction of acetone with hydrogen to form methyl ethyl ketone;

reaction of aromatic compounds with olefins to form alkylated aromatic compounds;

reaction of carbon monoxide with hydrogen to methanol and the like.

In carrying out the some of the processes, it will be appreciated that additional feed lines may be necessary. For example, in those reactions in which hydrogen or ammonia are present in the reaction zone, a feed is provided below the catalyst bed, preferably within the catalyst section. In a preferred operation the reactants, e.g. alcohol and olefin, are maintained within the column by feeding a sufficient amount of a lower boiling inert material which forms the overhead and reflux to the system to the exclusion of the reactants.

A catalytic distillation process employs a catalyst system (See U.S. Pat. Nos. 4,215,011 and 4,302,356) which provides for both reaction and distillation concurrently in the same reactor, at least in part, within the catalyst system. The method involved is briefly described as one where concurrent reaction and distillation occur in a combination of reactor-distillation structures which are described in several U.S. Patents, namely U.S. Pat. Nos. 4,242,530; 4,250,052; 4,232,177; 4,302,356; 4,307,254; and 4,336,407 which are incorporated herein in their entirety. Additionally U.S. Pat. Nos. 4,302,356 and 4,443,559 disclose catalyst structures which are useful as distillation structures.

For example, methanol and isoamylene (or the stream from the boiling point reactor which contains, ether, some unreacted isoolefin and methanol or make up methanol) containing $C_5$ stream are continuously fed to the distillation column reactor where they are contacted in the catalytic distillation structure. The methanol preferentially reacts with isoamylene, forming TAME which is heavier than the $C_5$ components of the feed and the methanol, hence it drops in the column to form the bottoms. Concurrently, the unreacted $C_5$'s (e.g., n-pentane, n-pentenes) are lighter and form an overhead. The olefins in the feeds to the reaction usually contain linear and branched olefins, e.g., n-butenes, isobutene, n-amylenes and isoamylenes. The alcohols are preferably monohydric, such as methanol, ethanol, propanol and mixtures thereof. The branched chained olefins are selectively more reactive and the reactions may be operated to favor their reaction, particularly the tertiary olefins as known in the art.

In a further embodiment having a common rectification section, an extractive solvent may be added during the reactions to the distillation column reactor to any or all sections of the column at a location above the feed but below the upper terminus of the incoming side and/or below the upper terminus but within or above a catalyst bed. It is understood that the extractive solvent would be at least 25° C. higher boiling than the product of the reaction and that extractive solvent would be at least 60° C. higher boiling than the first component described hereinabove. The extractive solvent should comprise at least 50 volume % of the internal liquid in order to be effective at altering relative volatilities in the column. Preferably the extractive solvent may be recovered and separated from the extracted material for recycle within the system.

Referring now to the drawings, an etherification carried out in the present apparatus operates generally as follows:

Section A distills ether in feed from unreacted alcohol and isolefins in feed. Non-reactive hydrocarbons that are more volatile than the ether are also removed from the ether. Vapor exits the top of the section A and enters the common rectification section B. Reflux to section A is provided from common rectification section B. The division of the reflux as to how much goes to zone "A" versus how much goes to zone "C" is intentionally designed for and is to be controlled.

Section B rectification section concentrates light components in feed that are purged as overhead product. Purging of lights is needed to control temperatures in catalytic distillation columns. Section B also controls the ether product level in purge to a very low level (ppm), and minimizes the loss of $C_5$'s to the overheads.

Figure 2:
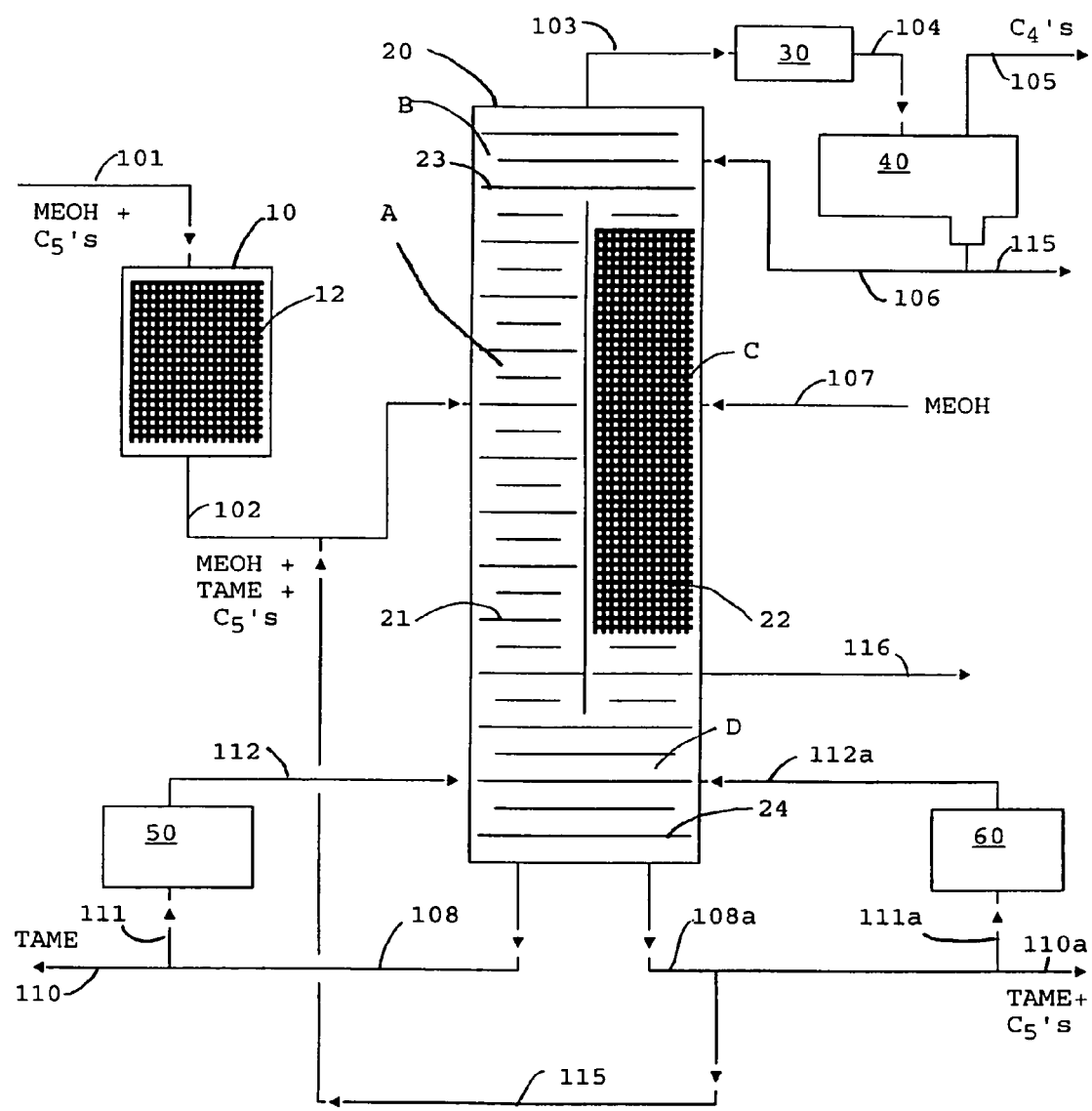
FIG. 2 is configuration of the present apparatus having a common stripping section in addition to a common rectification section.

Section C parallels section A and is fed via liquid reflux from the bottom of section B and vapor from stripping section D (if present) or reboiler (if section D is not present). If stripping section D is utilized (as in FIG. 2), the split of the vapor between side "A" and side "C" is intentionally controlled at prescribed levels using either active or passive engineering-design means. Catalytic distillation converts alcohol and isoolefin to ether in section C. Trays below the catalytic distillation zone strip MeOH from hydrocarbons and ether by using its azeotrope with the hydrocarbons. A stripping section "D" can be utilized as shown in FIG. 2. If so, a sidedraw 116 from section "C" below the catalyst bed but above the bottom of the divide can be utilized to pull off $C_5$'s with some accompanying TAME. It is advantageous to draw off the vapor as a sidedraw via conduit 116, and condense it downstream (not shown). This allows an essentially near $C_5$-free pure TAME product to be withdrawn from the bottom of the unit as stream 110a with minimal diverting of product TAME to the sidedraw conduit 116.

FIG. 1 shows a simplified flow diagram of a TAME process utilizing the present invention. The divided wall distillation column reactor 20 generally includes three sections: section A) containing a first distillation zone (stripping section) which contains inert distillation structure at the bottom to separate the TAME from unreacted methanol, reactive $C_5$ hydrocarbons and inerts; section C) a middle reaction zone containing the catalytic distillation structure, where the etherification occurs; and section B) an upper distillation zone (rectification section) containing inert distillation structure to separate back into the reaction zone any unreacted isoamylenes and some methanol. As noted methanol and $C_5$'s form an azeotrope. This azeotrope boils about 10 to 15° F. lower than the $C_5$'s and is thus predominantly in the upper distillation zone and overheads.

In a conventional distillation column reactor there is generally a reflux of condensed overheads to facilitate the separation of the more volatile unreacted components from the product. In the case of etherification of $C_5$ olefins with methanol to produce TAME, the overheads usually contain methanol, inert $C_5$'s (i.e., normal pentenes or pentanes) and other lighter inert materials which might be in the feed. The condensible overheads are recovered and the methanol is usually separated from the hydrocarbons as by water washing, the methanol being selectively removed in the water phase. The methanol and water may then be separated by distillation and the methanol recycled to the reactor.

The present divided wall column presents another solution. The condensed reflux containing methanol and $C_5$ olefins, which is comprised of the overheads from both sides of the column, descends into both sides of the column. In a first side the reflux without catalyst simply helps separate the product TAME from the unreacted methanol and $C_5$'s. However, in a second side, catalyst is loaded and the methanol and $C_5$ olefins react to produce additional TAME. The second side is operated to separate the methanol/$C_5$ azeotrope from the TAME/$C_5$ mixture. In the preferred mode, the reactor is operated "dead headed in methanol". This means that substantially all of the methanol entering the catalytic distillation unit is destined to be consumed by reaction with very little methanol (if any) leaving in any of the column effluent streams. Preferably, the total reactive-methanol requirements required by both fixed-bed prereactor and by the catalytic distillation reactor enter through conduit 101. This will allow for better conversion within the fixed bed prereactor, and satisfy the reactive stoichiometric requirements for the catalytic distillation column. Composition monitoring within section "C" is desirable to keep the methanol inventory in the column in good balance with the reactive needs. The total methanol feed rate to the reactive system is adjusted so as to maintain the methanol profile at near azeotrope composition across the catalyst yet avoid pushing methanol out of the lowermost conduits of the system so as to essentially keep methanol away from any withdrawn TAME-rich product. The net effect of the present invention is to integrate the benefits from both the catalytic distillation column and the divided wall column.

Catalysts preferred for the etherification process are resin cation exchangers, which contain sulfonic acid groups, and which have been obtained by polymerization or copolymerization of aromatic vinyl compounds followed by sulfonation. The resulting products preferably contain an average of 1.3 to 1.8 sulfonic acid groups per aromatic nucleus. Particularly, suitable polymers which contain sulfonic acid groups are copolymers of aromatic monovinyl compounds with aromatic polyvinyl compounds, particularly, divinyl compounds, in which the polyvinyl benzene content is preferably 1 to 20% by weight of the copolymer (see, for example, German Patent specification 908,247). The ion exchange resin is preferably used in a granular size of about 0.25 to 1 mm, although particles from 0.15 mm up to about 2 mm may be employed.

A preferred catalytic distillation structure for use herein comprises placing the cation exchange resin particles into porous containers which are surrounded by open space comprising 50-95 volume % of the structure. This allows the requisite flows and prevents loss of catalyst. Suitable structures are described in U.S. Pat. Nos. 5,266,546, 4,731,229, 5,073,236, 5,266,546, 5,431,890 and 5,730,843 which are incorporated by reference. The catalytic distillation structure when loaded into the column constitutes a distillation reaction zone.

Referring to FIG. 1, methanol and mixed $C_5$'s containing isoamylenes are fed via flow line 101 to the primary reactor 10 containing a bed of catalyst 12. The resin catalyst is loaded into the straight pass reactor 10 as a fixed bed of granules. The feed to the reaction is fed to the bed in liquid phase. U.S. Pat. Nos. 5,003,124 and 4,950,803 which are incorporated herein, disclose a liquid phase process for the etherification of $C_4$ to $C_6$ isoolefins with $C_1$ to $C_6$ alcohols in a boiling point straight pass reactor (boiling point reactor) that is controlled at a pressure to maintain the reaction mixture at its boiling point and where the effluent may be fed directly to a catalytic distillation reactor. The bed may be horizontal, vertical or angled with either upflow or downflow of the reactants and reaction products. Preferably the bed is vertical with the feed passing downward through the bed and exiting, after reaction, through the lower end of the reactor. In the reactor 10 a portion of the isoamylenes reacts with methanol to form tertiary amyl methyl ether (TAME) which exits the reactor 10 as effluent via flow line 102 along with unreacted methanol and $C_5$'s.

The effluent from the reactor in flow line 102 is fed into section A of a divided wall column. Section A comprises a zone 21 containing standard distillation structure such as sieve tray, bubble cap tray or packing. In the zone 21 the TAME is separated from unreacted methanol and $C_5$'s. The TAME is taken as bottoms via flow line 108 some of which is recycled through reboiler 50 via flow lines 111 and 112. TAME product is taken via flow line 110. Note that in the configuration shown as FIG. 2, the reboiler 50 and reboiler 60 may be combined into a single reboiler. Product streams 108 and 108a become as merged. Also as merged are streams 112 together with 112a. Finally, product stream 110 also becomes merged with stream 110a.

In all cases, the vapor traveling upwards in the column is purposely divided at the lowermost terminus of the dividing wall in a prescribed ratio as determined beforehand from rigorous reactive-distillation simulation of divided-wall configuration. Such division of flow may be controlled to prescribed values by engineering-design methods incorporating either active or passive means. Similarly, the liquid traveling down the column approaching the upper terminus is purposely divided as well in a manner consistent with goals established from same said reactive distillation simulation design exercises. Again, such division of flow is held at prescribed values using engineering design methods incorporating either active or passive means. These considerations are understood to be so in all cases.

In the section B the unreacted methanol and $C_5$'s are rectified in common rectification zone 23 to concentrate lighter boiling components such as $C_3$ and $C_4$ hydrocarbons in the vapor phase which are taken as overheads via flow line 103 and passed to partial condenser 30 and are then passed on to separator 40 via flow line 104. The lights are purged either as vapor via flow line 105 or as condensed liquid via flow line 115 or both. A portion the condensed liquid (including $C_5$'s and methanol) is fed back as reflux to common rectification section 23 via conduit 106. The removal of light components from zone 23 is important for controlling the temperature in section C.

Section C operates in parallel to section A and contains a catalytic distillation zone 22 where a portion of the unreacted isoamylenes react further with methanol to form additional TAME. Additional methanol to meet catalytic distillation reaction needs is co-fed way upstream within stream 101 or (optionally) co-fed via flow line 107 or a combination of both. The methanol feed rate is adjusted to maintain a near azeotropic composition across the bed. However, excess methanol beyond this feed rate which would result in methanol loss to product is to be avoided. In the distillation zone 22 below the catalyst bed but above the terminus working together and contiguously with the distillation zone 24, the unreacted methanol and isoamylenes are stripped from the the TAME/$C_5$ mixture which is taken as bottoms via flow line 108a. Some of the TAME/$C_5$ mixture is recycled through reboiler 60 via flow lines 111a and 112a. A product containing TAME and $C_5$'s is withdrawn via flow line 110a.

In summary the TAME product is separated from the methanol/$C_5$ azeotrope in section A, lights are removed from methanol/$C_5$ in section B and TAME and $C_5$'s are separated from the methanol/$C_5$'s in section C while reacting methanol with isoamylenes in the second side. Because only enough methanol is added to make up for that reacted and to support the azeotropes in the system, there is no need for additional process equipment normally associated with separating methanol from $C_5$ mixtures.

FIG. 2 shows an integrated distillation and catalytic distillation system similar to FIG. 1 except that a common stripping section D replaces the two separate stripping sections and a single bottoms is recovered.

As methanol previously, the bulk of the $C_5$s accompanied by some TAME can (optionally) be taken as a sidedraw 116 as illustrated in both FIG. 1 and FIG. 2. A vapor sidedraw is preferred as it can be richer in $C_5$s and leaner in TAME. Said vapor drawoff may be condensed in an external condenser and knockout pot which is routed to product storage. With such configuration, it becomes possible to recover an essentially pure TAME stream as a bottoms product.

The invention claimed is:

1. A distillation column having;
    at least two vertical distillation sections, at least one of said sections containing catalyst and at least one of said sections being free of catalyst;
    at least one wall separating the at least one catalysts-containing section from the at least one section free of catalyst, the wall extending through a vertical portion of said distillation column, said vertical portion comprising less than the total height of said column and said sections having a common rectification section above said vertical distillation sections and being in fluid communication around an upper vertical terminus of said wall; and
    consisting of means for adding an extractive solvent to at least one of said catalyst-containing sections, wherein said means for adding an extractive solvent is below said upper terminus and selected from one of above a feed, within said catalyst, and above said catalyst.

2. The distillation column according to claim 1 wherein said means for adding an extractive solvent is above a feed.

3. The distillation column according to claim 1 wherein said means for adding an extractive solvent is within said catalyst.

4. The distillation column according to claim 1 wherein said means for adding an extractive solvent is above said catalyst.

* * * * *